United States Patent [19]

Meriwether

[11] Patent Number: 4,490,354

[45] Date of Patent: Dec. 25, 1984

[54] ANTIPERSPIRANT METHOD CONTAINING VANADIUM SALTS

[75] Inventor: Lewis S. Meriwether, Wilton, Conn.

[73] Assignee: American Cyanamid Company, Stamford, Conn.

[21] Appl. No.: 259,746

[22] Filed: May 1, 1981

Related U.S. Application Data

[63] Continuation-in-part of Ser. No. 139,364, Apr. 11, 1980, abandoned.

[51] Int. Cl.³ .......................... A61K 7/32; A61K 7/34; A61K 7/36; A61K 7/38
[52] U.S. Cl. ................................ 424/65; 424/DIG. 5; 424/47; 424/66; 424/67; 424/68; 424/69; 424/168
[58] Field of Search .......................................... 424/65

[56] References Cited

U.S. PATENT DOCUMENTS

| | | | |
|---|---|---|---|
| 1,066,615 | 7/1913 | Hitchcock | 424/287 |
| 2,135,111 | 11/1938 | Prebluda | 424/287 |
| 2,236,387 | 3/1941 | Wallace, Jr. et al. | 424/287 |
| 3,076,830 | 2/1963 | Conn | 260/429 |
| 3,172,817 | 3/1965 | Leupold et al. | 424/65 |
| 3,803,189 | 4/1974 | Haglid | 260/429 R |
| 4,055,655 | 10/1977 | Maurer et al. | 424/294 |
| 4,112,085 | 9/1978 | Morelle et al. | 424/287 |

OTHER PUBLICATIONS

Sagarin, Cosmetics Science & Technology, 9/1957, pp. 270 to 273.

Primary Examiner—Dale R. Ore
Attorney, Agent, or Firm—Charles J. Fickey

[57] ABSTRACT

A composition for inhibiting perspiration on the skin comprising a selected, water-soluble vanadium salt and a cosmetically acceptable compatible carrier.

6 Claims, No Drawings

ANTIPERSPIRANT METHOD CONTAINING VANADIUM SALTS

This is a continuation-in-part of Ser. No. 06/139,364, filed 04/11/80, now abandoned.

This invention relates generally to astringent metal salts useful in antiperspirant compositions. More particularly, it relates to the use of certain vanadium salts in antiperspirants.

Many astringent materials are known in the art for treating skin areas in order to eliminate or inhibit perspiration, such as aluminum sulfate, aluminum chloride, aluminum chlorhydrate, zinc sulfate and corresponding sulfocarbamates; zirconium chlorhydrate and other zirconium salts; and combinations of any of these salts.

In general, the particular astringent metal salt selected will depend, to a certain extent, on the area of the body to be treated, e.g., the axilla, the feet, or the body generally.

A particularly excellent class of metal salts has now been discovered to be useful in inhibiting or preventing perspiration on the skin. Certain salts of vanadium have been found which demonstrate a high level of long acting sweat suppression when applied to the skin. These salts are the water soluble salts of vanadium wherein the vanadium has a valance number of 3, 4 or 5. By "water-soluble" is meant that the salt is soluble in water to an extent equal to at least about one percent (1%). Such vanadium salts include, for example, $VOCl_2$, $VOBr_2$, $VOCl_3$, $VOBr_3$, $VCl_3$, $VBr_3$, $VO(NO_3)_2$ and $VO(ClO_4)_2$ and the like.

In addition to the use of these vanadium salts alone, mixtures of the vanadium salts and mixtures of same with other astringent salts, such as, for example, aluminum chloride, bromide, chlorhydrate, nitrate and perchlorate, and zirconyl chloride, bromide, nitrate, perchlorate, carbonate and acetate, zinc chloride, sulfate and phenolsulfonate, and the like, are possible.

In accordance with the present invention, the water-soluble vanadium salts are incorporated into compositions comprising the salt and a cosmetically acceptable compatible carrier. By "cosmetically acceptable compatible carrier" is meant any material, or combination of materials, which aids in the delivery of the vanadium salt to the skin area to be treated, is cosmetically non-offensive from a consumer standpoint, and does not materially adversely interfere with the antiperspirant activity of the vanadium salt. Numerous compounds and systems meet these criteria and the use of same is well known to the art. Exemplary carriers are: water, lower alkyl alcohols such as ethanol and isopropanol, natural waxes, such as beeswax, spermaceti and cresin, hydrocarbon waxes, hydrocarbon oils such as mineral oil, $C_{12-22}$ straight chain alcohols and fatty acids, volatile silicones, suspending agents such as talc and starch, halogenated hydrocarbons such as trichloromonofluoromethane, dichloro-difluoromethane and dichloro-tetrafluoroethane, and the like. Obviously, compatible combinations of these carriers may also be used.

Of course, other additives may be incorporated into the compositions, such as, for example, fragrances, dispersing agents, binding agents, color-masking agents and the like, depending, inter alia, upon the type of product into which the vanadium salt is to be incorporated.

Although the water-soluble vanadium salt may comprise virtually any amount of the composition, it preferably comprises from about 3 to 30%, by weight, thereof. When the vanadium salt is used in combination with another, known antiperspirant salt, this other salt is generally present in a ratio of from about 1 to 10 parts for each 1 part of vanadium salt. However, these ratios are by no means critical and suitable ratios will depend, inter alia, upon the particular salt combinations being used.

The vanadium salts of the instant invention may be formulated into all types of antiperspirant products, such as, for example, roll-ons, sticks, creams, lotions and aerosols, whether used in the form of a solid, liquid or spray.

The vanadium salts of the instant invention are particularly advantageous for skin application usage due to their very low toxicity and skin irritation levels. Furthermore, these water-soluble salts do not accelerate cell division in the skin, as is the case, for example, with zirconium salts. As a result, the salt plug which is formed in the sweat duct is less rapidly expelled therefrom and a correspondingly slower recovery of perspiration is noted.

The comparative effectiveness of vanadium salts of the present invention vis-a-vis other known antiperspirant salts is set forth in Tables I and II, wherein it is clearly shown that the vanadium salts are highly efficacious in inhibiting perspiration.

TABLE I

Forearm Antiperspirant Test Results on Certain Vanadium, Aluminum and Zirconium Salts and Mixtures

| Salt (20% w/w aqueous) | Percent Sweat Reduction* After 24 Hours | After 7 Days |
|---|---|---|
| $VOCl_3$ | 98 | 83 |
| $VOBr_2$ | 93 | 81 |
| $VOCl_2$ | 93 | 60 |
| $VOCl_2$ (10%) | 83 | 60 |
| $VO(ClO_4)_2$ | 68 | 70 |
| $VOSO_4$ | 15 | 0 |
| $VCl_3$ | 95 | 80 |
| $AlCl_3$ | 93 | 78 |
| $Al(NO_3)_3$ | 60 | 43 |
| $Al_2(OH)_5Cl$ | 68 | 38 |
| $ZrOCl_2$ | 88 | 8 |
| $ZrO(NO_3)_2$ | 65 | 33 |
| 6:1 Al/Zr complex | 68 | 30 |
| 10:1 Al/Zr complex | 78 | 45 |

*An occlusive patch containing 200 μl of test solution was applied to 1 cm² of skin for 3 hours. Thermally induced sweating patterns were assayed using a silicone rubber replicate technique. Averages of 6 panelists.

TABLE II

Comparative Antiperspirant Data On Vanadium Salts Of The Present Invention And Other Known Antiperspirant Salts

| Salt | Conc. (% aqueous) | Percent Sweat Reduction* 24 hrs. | 7 days |
|---|---|---|---|
| $VOCl_2$ | 20 | 93,88 | 60,80 |
| $VOCl_2$ | 10 | 83 | 60 |
| $VOCl_2$ | 5 | 38 | 23 |
| $VOCl_2$ Roll-on | 12.5 | 93 | 83 |
| $VOBr_2$ | 20 | 88 | 81 |
| $VO(ClO_4)_2$ | 20 | 68 | 70 |
| $VOSO_4$ | 20 | 68 | 43 |
| $VCl_3$ | 20 | 95 | 80 |
| $VOCl_3$ | 20 | 98 | 83 |
| ACH/$VOCl_2$ (10:1) | 25 | 54 | 27 |
| ACH/$VOCl_2$ (6:1) | 25 | 48 | 38 |
| ACH/$VOCl_2$ (4:1) | 25 | 58 | 63 |
| ACH/$VOCl_2$ (2:1) | 25 | 71 | 65 |
| $AlCl_3$/$VOCl_2$ (10:1) | 25 | 90 | 85 |
| $ZrOCl_2$/$VOCl_2$ (10:1) | 25 | 88 | 75 |
| ACH/$ZrOCl_2$ (6:1) | 20 | 68 | 30 |
| $AlCl_3$ | 25 | 93 | 78 |

TABLE II-continued

Comparative Antiperspirant Data On Vanadium Salts Of The Present Invention And Other Known Antiperspirant Salts

| Salt | Conc. (% aqueous) | Percent Sweat Reduction* 24 hrs. | 7 days |
|---|---|---|---|
| ACH | 25 | 68 | 45 |

*3-hour occlusion on forearm, sweat reduction measured after 24 hours and 7 days using silicone replicate method.

The following examples illustrate the use of vanadium salts of the present invention in various antiperspirant compositions. All parts and percentages are by weight unless otherwise noted.

EXAMPLE 1

| Composition of Aqueous Roll-On Antiperspirant | |
|---|---|
| Arlacel 165 (glycerol monostearate), made by ICI United States, Inc. | 4.3% |
| Standamul G (octyl dodecanol), Henkel, Inc. | 1.1 |
| Mineral Oil (white, 50 viscosity) | 4.3 |
| Promulgen G (Cetyl alcohol and propoxylated cetyl alcohol), Robinson-Wagner Company, Inc. | 1.1 |
| Veegum K (Siliceous dispersing agent), R. T. Vanderbilt Chemicals Company | 1.0 |
| Propylene glycol | 4.0 |
| Vanadyl chloride (VOCl$_2$) | 12.5 |
| Fragrance | 0.2 |
| Water | 75.8 |

EXAMPLE 2

| Hydroalcoholic Antiperspirant Roll-On Composition | |
|---|---|
| Ethanol | 60% |
| Propylene Glycol | 8 |
| VO(NO$_3$)$_2$ | 12 |
| Water | 20 |

EXAMPLE 3

| Antiperspirant Powder Composition | |
|---|---|
| Talc | 78% |
| Corn Starch | 10 |
| VO(ClO$_4$)$_2$ | 10 |
| Boric Acid | 2 |

EXAMPLE 4

| Cream Antiperspirant Composition | |
|---|---|
| VOCl$_3$ | 15% |
| Glycerol | 5 |
| Water | 60 |
| Glyceryl Monostearate | 15 |
| Spermaceti | 5 |

EXAMPLE 5

| Stick Antiperspirant Composition | |
|---|---|
| VOSO$_4$ | 35% |
| Propylene Glycol | 20 |
| Stearyl Amide | 20 |
| Anhydrous Alcohol (SDA 39C) | 12 |
| Isopropyl Myristate | 2.2 |
| Isocetyl Alcohol | 10.8 |

EXAMPLE 6

| Suspension-Type Aerosol Antiperspirant Composition | |
|---|---|
| VOBr$_3$ | 4% |
| Cab-O-Sil M-5 (Siliceous dispersing agent), Cabot Corporation | 0.4 |
| Isopropyl Myristate | 8 |
| Perfume | 0.3 |
| Propellant A-31 (Isobutane) | 87.3 |

EXAMPLE 7

| Alcohol-Based Aerosol Antiperspirant Composition | |
|---|---|
| VCl$_3$ | 9% |
| Isopropyl Palmitate | 2.7 |
| Alcohol (SD-40 Anhydrous) | 34.2 |
| Crodafos N-10 Acid 0.8 (phosphated oleyl ether), Croda Inc. | 0.8 |
| Crodafos N-10 Neutral (phosphated oleyl ether), Croda, Inc. | 0.8 |
| Trimethylolpropane | 2.5 |
| Trichloromonofluoromethane | 50 |

EXAMPLE 8

| Pump Spray Antiperspirant Composition | |
|---|---|
| VBr$_3$ | 15% |
| Anhydrous Alcohol (SDA 39C) | 81 |
| Isopropyl Myristate | 1 |
| Stearic Acid | 3 |

What is claimed is:

1. A method of inhibiting perspiration on the skin which comprises topically administering to the skin a water-soluble vanadium salt wherein the vanadium has a valance number of 3, 4 or 5.

2. The method of claim 1 wherein the vanadium salt is in a composition comprising said salt and a cosmetically acceptable compatible carrier.

3. The method of claim 2 wherein the vanadium salt comprises from about 3 to +percent, by weight, of the composition.

4. The method of claim 2 or claim 3 wherein the carrier is water.

5. The method of claim 2 or claim 3 wherein the vanadium salt is selected from the group consisting of VOCl$_2$, VOBr$_2$, VOCl$_3$, VOBr$_3$, VCl$_3$, VBr$_3$, VO(NO$_3$)$_2$ and VO(Cl0$_4$)$_2$.

6. The method of claim 2 or claim 3 wherein the composition further comprises at least one additional astringent metal salt.

* * * * *